United States Patent
Zhang et al.

(10) Patent No.: US 10,528,714 B2
(45) Date of Patent: Jan. 7, 2020

(54) METHOD AND APPARATUS FOR AUTHENTICATING USER USING ELECTROCARDIOGRAM SIGNAL

(71) Applicant: Samsung Electronics Co., Ltd., Suwon-si (KR)

(72) Inventors: Chao Zhang, Beijing (CN); Haixiao Liu, Beijing (CN); Yang Liu, Beijing (CN); Chisung Bae, Yongin-si (KR); Sang Joon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/867,147

(22) Filed: Jan. 10, 2018

(65) Prior Publication Data
US 2018/0196932 A1   Jul. 12, 2018

(30) Foreign Application Priority Data

Jan. 11, 2017  (CN) .......................... 2017 1 0019864
Nov. 10, 2017  (KR) ....................... 10-2017-0149410

(51) Int. Cl.
| | | |
|---|---|---|
| G05B 19/00 | (2006.01) | |
| G05B 23/00 | (2006.01) | |
| G06F 7/00 | (2006.01) | |
| G06F 7/04 | (2006.01) | |
| G08B 29/00 | (2006.01) | |
| G08C 19/00 | (2006.01) | |
| H04B 1/00 | (2006.01) | |

(Continued)

(52) U.S. Cl.
CPC ............ *G06F 21/32* (2013.01); *A61B 5/0452* (2013.01); *A61B 5/7264* (2013.01); *A61B 5/04012* (2013.01); *A61B 5/117* (2013.01); *G06K 2009/00939* (2013.01)

(58) Field of Classification Search
CPC .. G06F 21/32; G06K 9/00536; G06K 9/6271; G06K 9/4628; G06K 2009/00939; A61B 5/7264; A61B 5/0452; A61B 5/04012; A61B 5/117
USPC ....................................................... 340/5.82
See application file for complete search history.

(56) References Cited

U.S. PATENT DOCUMENTS

| 8,046,058 B2 | 10/2011 | Lin et al. |
| 8,994,498 B2 | 3/2015 | Agrafioti et al. |

(Continued)

FOREIGN PATENT DOCUMENTS

| KR | 10-1570679 B1 | 11/2015 |
| KR | 10-1587874 B1 | 1/2016 |

(Continued)

*Primary Examiner* — Tanmay K Shah
(74) *Attorney, Agent, or Firm* — NSIP Law

(57) ABSTRACT

A method and apparatus to authenticate a registered user are described. The method and apparatus include a processor configured to identify a first electrocardiogram (ECG) signal measured from the user, and determine a similarity between the first ECG signal and a second ECG signal based on the identified first ECG signal and the second ECG signal included in a reference ECG signal set. The processor is also configured to determine an authentication threshold corresponding to the reference ECG signal set, and determine whether to authenticate the first ECG signal measured from the user by comparing the determined similarity and the authentication threshold.

20 Claims, 6 Drawing Sheets

(51) Int. Cl.
   *H04B 3/00*      (2006.01)
   *H04Q 9/00*      (2006.01)
   *G06F 21/32*     (2013.01)
   *A61B 5/0452*    (2006.01)
   *A61B 5/00*      (2006.01)
   *G06K 9/00*      (2006.01)
   *A61B 5/117*     (2016.01)
   *A61B 5/04*      (2006.01)

(56) References Cited

U.S. PATENT DOCUMENTS

| | | |
|---|---|---|
| 9,231,765 B2 | 1/2016 | Flautner et al. |
| 2015/0373019 A1 | 12/2015 | El Saddik et al. |
| 2016/0042219 A1 | 2/2016 | Bae et al. |
| 2016/0191517 A1 | 6/2016 | Bae et al. |
| 2016/0232340 A1 | 8/2016 | Feng et al. |
| 2017/0242974 A1* | 8/2017 | Zhao .................... A61B 5/0452 |

FOREIGN PATENT DOCUMENTS

| | | |
|---|---|---|
| KR | 10-2016-0088047 A | 7/2016 |
| KR | 10-1646566 B1 | 8/2016 |
| KR | 10-1657005 B1 | 9/2016 |

\* cited by examiner

METHOD AND APPARATUS FOR AUTHENTICATING USER USING ELECTROCARDIOGRAM SIGNAL

CROSS-REFERENCE TO RELATED APPLICATIONS

This application claims the benefit under 35 USC § 119(a) of Chinese patent Application No. 201710019864.1 filed on Jan. 11, 2017 in the State of Intellectual Property Office of the People's Republic of China and Korean Patent Application No. 10-2017-0149410 filed on Nov. 10, 2017 in the Korean Intellectual Property Office, the entire disclosures of which are incorporated herein by reference for all purposes.

BACKGROUND

1. Field

The following description relates to a method and apparatus to authenticate a user using an electrocardiogram (ECG) signal.

2. Description of Related Art

Authentication technology using biometric recognition identifies a user based on inherent biological characteristics or behavioral characteristics of an individual, for example, an iris, a fingerprint, voice, a vein pattern, and a gait. Biometric characteristics used to authenticate differ for each person, but remain on average consistent through the person's lifetime. Biometric recognition technology represents a technique to authenticate the person by extracting a signal or data associated with a biometric characteristic of the person and comparing the extracted signal or data to previously stored data.

Further, authenticating using biometric characteristics, such as electrocardiogram (ECG) signal-based user authentication, are not easily falsified and have a relatively high stability and high identification rates. Accordingly, the ECG signal-based user authentication research is ongoing.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an example, there may be provided a method of authenticating a user, including: identifying a first electrocardiogram (ECG) signal measured from the user; determining a similarity between the first ECG signal and a second ECG signal based on the identified first ECG signal and the second ECG signal included in a reference ECG signal set; determining an authentication threshold corresponding to the reference ECG signal set; and determining whether to authenticate the first ECG signal measured from the user by comparing the determined similarity and the authentication threshold.

The determining of the authentication threshold may include: determining an authentication threshold model corresponding to the reference ECG signal set; and acquiring the authentication threshold by applying a feature vector of the reference ECG signal set to the determined authentication threshold model.

The feature vector may be extracted from the preprocessed second ECG signal through a neural network.

The authentication threshold has a positive correlation with any one or any combination of a number of second ECG signals included in the reference ECG signal set.

The determining of whether to authenticate may include determining that an authentication may be a success in response to a maximum similarity among the one or more similarities being greater than the authentication threshold, or determining that the authentication may be a failure in response to the maximum similarity being less than or equal to the authentication threshold.

The method further including: updating the reference ECG signal set in response to the authentication being determined as the success, and wherein the updating may include updating the reference ECG signal set using the first ECG signal in response to the maximum similarity being greater than an update threshold of the reference ECG signal set.

The method further including: updating the reference ECG signal set in response to the authentication being determined as the failure, wherein the updating may include updating the reference ECG signal set using the first ECG signal in response to the user being authenticated using an authentication method excluding an ECG signal-based user authentication.

The authentication of the user by the authentication method excluding the ECG signal-based user authentication may be performed in response to a number of updates being less than a preset threshold.

The updating of the reference ECG signal set using the first ECG signal may include adding the authenticated first ECG signal to the reference ECG signal set as the second ECG signal in response to a number of second ECG signals included in the reference ECG signal set being less than a preset number, or coupling the measured first ECG signal and the second ECG signal indicating the maximum similarity in response to the number of second ECG signals included in the reference ECG signal set being greater than or equal to the preset number.

The updating of the reference ECG signal set using the first ECG signal may include adding the unauthenticated first ECG signal to the reference ECG signal set as the second ECG signal in response to a number of second ECG signals included in the reference ECG signal set being less than a preset number, or adding the first ECG signal to the reference ECG signal set instead of using the second ECG signal corresponding to a maximum similarity sum between the second ECG signal and other second ECG signals included in the reference ECG signal set in response to the number of second ECG signals included in the reference ECG signal set being greater than or equal to the preset number.

The coupling may include coupling the first ECG signal and the second ECG signal based on a weight of the first ECG signal and a weight of the second ECG signal having a maximum similarity with the first ECG signal in the reference ECG signal set.

In accordance with an example, there may be provided a non-transitory computer-readable storage medium storing instructions that, when executed by a processor, cause the processor to perform the method described above.

In accordance with an example, there may be provided an apparatus to authenticate a user, including: a processor configured to: identify a first electrocardiogram (ECG) signal measured from the user, determine a similarity between the first ECG signal and a second ECG signal based on the identified first ECG signal and the second ECG signal included in a reference ECG signal set, determine an authentication threshold corresponding to the reference ECG signal set, and determine whether to authenticate the first ECG signal measured from the user by comparing the determined similarity and the authentication threshold.

The data encoding apparatus may also include a memory configured to store instructions, wherein the processor may be further configured to execute the instructions to configure the processor to identify the first ECG signal measured from the user, determine the similarity between the first ECG signal and the second ECG signal based on the identified first ECG signal and the second ECG signal included in the reference ECG signal set, determine the authentication threshold corresponding to the reference ECG signal set, and determine whether to authenticate the first ECG signal measured from the user by comparing the determined similarity and the authentication threshold.

The processor may be configured to determine an authentication threshold model corresponding to the reference ECG signal set, and to acquire the authentication threshold by applying a feature vector of the reference ECG signal set to the determined authentication threshold model.

The authentication threshold has a positive correlation with any one or any combination of a number of second ECG signals included in the reference ECG signal set.

The processor may be configured to determine that an authentication may be a success in response to a maximum similarity among the one or more similarities being greater than the authentication threshold, or to determine that the authentication may be a failure in response to the maximum similarity being less than or equal to the authentication threshold.

The processor may be configured to update the reference ECG signal set in response to the authentication being determined as the success, and to update the reference ECG signal set using the first ECG signal in response to the maximum similarity being greater than an update threshold of the reference ECG signal set.

The processor may be configured to update the reference ECG signal set in response to the authentication being determined as the failure, and to update the reference ECG signal set using the first ECG signal in response to the user being authenticated using an authentication method excluding an ECG signal-based user authentication.

In the case of updating the reference ECG signal set using the first ECG signal, the processor may be configured to add the authenticated first ECG signal to the reference ECG signal set as the second ECG signal in response to a number of second ECG signals included in the reference ECG signal set being less than a preset number, or couple the measured first ECG signal and the second ECG signal indicating the maximum similarity in response to the number of second ECG signals included in the reference ECG signal set being greater than or equal to the preset number.

In the case of updating the reference ECG signal set using the first ECG signal, the processor may be configured to add the unauthenticated first ECG signal to the reference ECG signal set as the second ECG signal in response to a number of second ECG signals included in the reference ECG signal set being less than a preset number, or to add the first ECG signal to the reference ECG signal set instead of using the second ECG signal corresponding to a maximum similarity sum between the second ECG signal and other second ECG signals included in the reference ECG signal set in response to the number of second ECG signals included in the reference ECG signal set being greater than or equal to the preset number.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
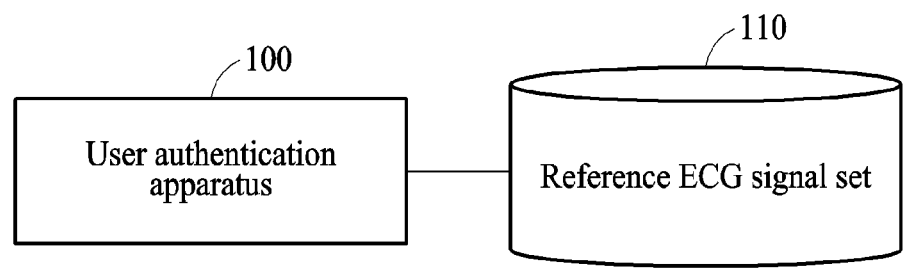
FIG. 1 is a diagram illustrating an example of authenticating a user using an electrocardiogram (ECG) signal.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The following structural or functional descriptions are exemplary to merely describe the examples, and the scope of the examples is not limited to the descriptions provided in the present specification. Various changes and modifications can be made thereto by those of ordinary skill in the art.

Although terms of "first" or "second" are used to explain various components, the components are not limited to the terms. These terms should be used only to distinguish one component from another component. For example, a "first" component may be referred to as a "second" component, or likewise, and the "second" component may be referred to as the "first" component within the scope of the right according to the concept of the present disclosure.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the singular forms are intended to include the plural forms as well, unless the context clearly indicates otherwise. It should be further understood that the terms "comprises/includes" and/or "comprising/including," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined herein, all terms used herein including technical or scientific terms have the same meanings as those generally understood by one of ordinary skill in the art. Terms defined in dictionaries generally used should be construed to have meanings matching with contextual meanings in the related art and are not to be construed as an ideal or excessively formal meaning unless otherwise defined herein.

The following examples may be used to recognize a fingerprint of a user. For instance, an operation of recognizing a fingerprint of a user is used to conduct an operation of authenticating or identifying the user. The operation of authenticating the user includes an operation of determining whether the user is a registered user. In this example, a result of the operation of authenticating the user is output to be true or false. The operation of identifying the user may include, for example, an operation of determining to which registered user the user corresponds among a plurality of registered users. In this example, a result is output of the operation of identifying the user as an identifier (ID) of any one registered user. If the user corresponds to none of the registered users, a signal is output indicating that the user is not identified.

The examples may be embodied using various hardware products, for example, a personal computer (PC), a laptop computer, a tablet computer, a smartphone, a television (TV), a smart electronic device, a smart vehicle, a kiosk, a wearable device, and the like. For example, the examples may be applied to authenticating a user in a smartphone, a mobile device, a smart home system, and the like. The examples may be applied to a payment service through a user authentication. Also, the examples may be applied to a smart vehicle system that automatically starts a vehicle by authenticating a user. Hereinafter, the examples will be described with reference to the accompanying drawings, and like reference numerals in the drawings refer to like elements throughout.

FIG. 1 is a diagram illustrating an example of authenticating a user using an electrocardiogram (ECG) signal.

FIG. 1 illustrates a user authentication apparatus 100 and a reference ECG signal set 110. The user authentication apparatus 100 refers to an apparatus that performs authentication of an identity of a user (hereinafter, also referred to as user authentication) using an ECG signal. For example, the user authentication apparatus 100 measures an ECG signal and performs user authentication. Hereinafter, a first ECG signal is used to distinguish the ECG signal of the user measured by the user authentication apparatus 100 from another ECG signal.

In one example, the user authentication apparatus 100 may be embedded in, for example, a mobile phone, a cellular phone, a smartphone, a personal computer (PC), a laptop computer, a notebook, a netbook, a tablet, a personal digital assistant (PDA), a digital camera, a game console, an MP3 player, a personal multimedia player (PMP), an electronic book (E-book), a navigation, a disk player, a set-top box, a home electronic appliance, a communication device, a display device, or another electronic device, or may interwork therewith. Also, a voice recognition apparatus may be embedded in, for example, a smart electronic device, a smart vehicle, an autonomous driving device, a smart home environment, a smart building environment, a smart office environment, or a smart electronic security system, or may interwork therewith. The user authentication apparatus 100 may be included in a wearable device that may be provided to a body of the user and may operate, or may interwork with the wearable device. The wearable device may be in a form of, for example, a ring, a watch, glasses, a bracelet, a belt, a band, a necklace, an ear ring, a helmet, or clothing.

The reference ECG signal set 110 includes one or more ECG signals used to authenticate the user using the first ECG signal measured by the user authentication apparatus 100. A reference ECG signal indicates an ECG signal used when the user authentication apparatus 100 performs the user authentication. Hereinafter, the reference ECG signal is referred to as a second ECG signal to be distinguished from another ECG signal.

The second ECG signal is an ECG signal of the user in each of various states. For example, the second ECG signal represents an ECG signal initially registered by the user, an ECG signal when the user is exercising, an ECG signal when the user is in a tranquil state, an ECG signal when the user is in an excited state, an ECG signal when the user is in an alcohol-drunk state. The ECG signal is updated several times using an authenticated ECG signal after predetermined time intervals.

The second ECG signal of the reference ECG signal set is stored as one of the ECG signal, in a form of a feature vector of the second ECG signal, in a form of a key point extracted from the second ECG signal, and in other suitable forms.

For example, the user authentication apparatus 100 extracts a feature vector by processing an ECG signal measured from the user to use as the second ECG signal. The user authentication apparatus 100 executes processing of the ECG signal, for example, filtering, a key point extraction, and segmentation of the ECG signal. The user authentication apparatus 100 extracts the feature vector using, for example, a trained neural network.

The user authentication apparatus 100 identifies the first ECG signal measured from the user to be authenticated. The user authentication apparatus 100 identifies the first ECG signal using an embedded sensor, or identifies the first ECG signal using an external sensor thereto or other devices. The external sensor to the user authentication apparatus 100 communicates wire or wirelessly with the user authentication apparatus 100 to transmit the first ECG signal. In one example, the user authentication apparatus 100 periodically requests the first ECG signal or, once the external sensor detects the first ECG signal, the external sensor automatically transmits the first ECG signal to the user authentication apparatus 100. The user authentication apparatus 100 identifies the first ECG signal measured from the user using other appropriate schemes.

The user authentication apparatus 100 identifies the first ECG signal measured from the user in response to a process or a manipulation that requires user authentication. For example, the process that requires the user authentication includes a screen unlock, a payment progress, and opening of an encrypted file.

The user authentication apparatus 100 determines whether to authenticate the user by comparing the first ECG signal and one or more second ECG signals included in the reference ECG signal set 110. For example, the user authentication apparatus 100 determines a similarity between the first ECG signal and each of one or more second ECG signals included in the ECG signal set 110, and determines whether to authenticate the first ECG signal measured from the user by comparing a maximum similarity among the determined similarities and an authentication threshold used for the user authentication.

The reference ECG signal set 110 is updated based on whether the authentication of the first ECG signal is a success or a failure, that is, whether the first ECG signal is successfully authenticated. For example, in response to the first ECG signal being successfully authenticated, the reference ECG signal set 110 is updated by adding the authenticated first ECG signal to the reference ECG signal set 110 or by coupling the authenticated first ECG signal and the existing second ECG signal. As another example, in response to the user being authenticated using another process regardless of a failure in authenticating the first ECG signal, the reference ECG signal set 110 is updated by adding the unauthenticated first ECG signal to the reference ECG signal set 110 or by replacing the existing second ECG signal with the unauthenticated first ECG signal.

The user authentication apparatus 100 accumulatively updates the reference ECG signal set 110 to reflect various states of the user. Accordingly, the accuracy of authentication performed by the user authentication apparatus 100 is enhanced.

Figure 2A:
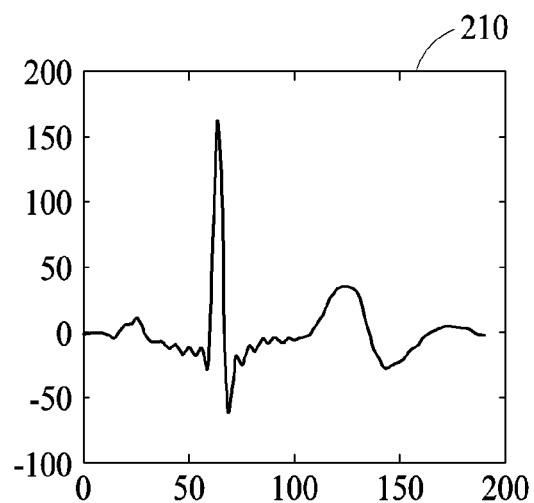
FIGS. 2A and 2B are graphs showing examples of an ECG signal of the same user in a different state.
Figure 2B:
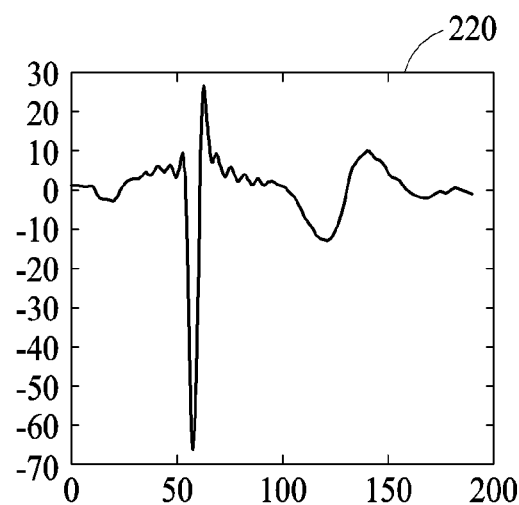

FIGS. 2A and 2B are graphs 210 and 220 showing examples of an ECG signal of the same user in a different state.

Compared to a facial recognition, a fingerprint recognition, and a voice recognition, it is relatively difficult to forge an ECG signal. However, even an ECG signal acquired from the same user may vary based on a state of the user. For example, an ECG signal acquired from the same user may show a great difference in various states. For example, an ECG signal before or after exercise, an ECG signal before or after a meal, and an ECG signal before or after a mood variation may be slightly different or significantly different.

The graph 210 of FIG. 2A relates to a first ECG signal and the graph 220 of FIG. 2B relates to a second ECG signal. For example, the second ECG signal is an existing ECG signal registered from the user and the first ECG signal is an ECG signal measured from the user by the user authentication apparatus 100 of FIG. 1.

A reference ECG signal set includes one or more second ECG signals. For example, the reference ECG signal set includes a single second ECG signal that is an ECG signal initially registered by the user, and includes a plurality of second ECG signals by registering and updating another second ECG signal.

Referring to the graphs 210 and 220 FIGS. 2A and 2B, even in the case of being the same user, the first ECG signal and the second ECG signal may have a relatively small similarity therebetween because the first ECG signal and the second ECG signal are ECG signals acquired in different physiological states or different mental states. Accordingly, the user authentication apparatus 100 compares the first ECG signal and the second ECG signal and recognizes the first ECG signal and the second ECG signal as ECG signals acquired from different users.

The user authentication apparatus 100 updates the reference ECG signal set by performing ECG signal authentication a number of times. Accordingly, the reference ECG signal set includes one or more second ECG signals. The user authentication apparatus 100 determines a similarity between the first ECG signal and each of one or more second ECG signals. In an example, the user authentication apparatus 100 determines that the authentication is a success in response to a maximum similarity among the similarities being greater than a preset or predefined authentication threshold, or determines that the authentication is a failure in response to the maximum similarity being less than or equal to the authentication threshold.

The authentication threshold, as a threshold of a similarity for successfully authenticating the first ECG signal, is, for example, a preset value or a value that is determined by the user authentication apparatus 100 based on the reference ECG signal set.

Figure 3:
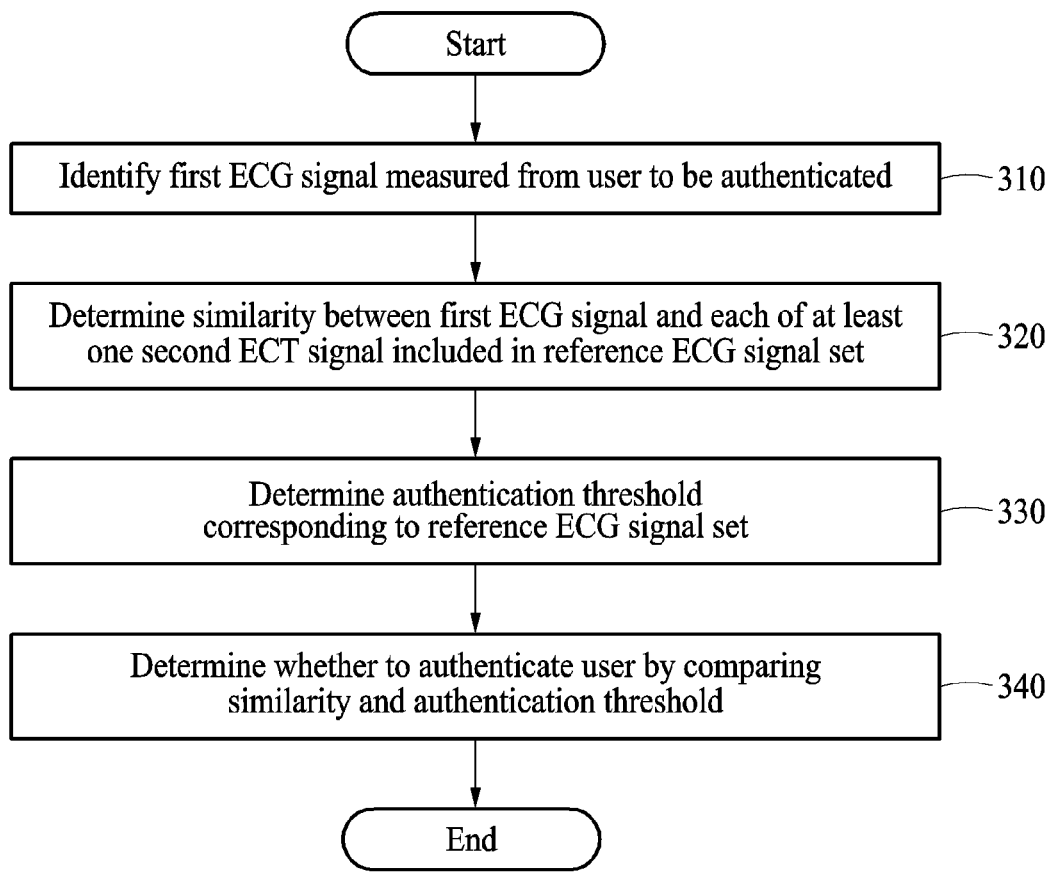
FIG. 3 is a flowchart illustrating an example of a user authentication method performed by a user authentication apparatus using an ECG signal.

FIG. 3 is a flowchart illustrating an example of a user authentication method using an ECG signal that is performed by a user authentication apparatus, such as the user authentication apparatus 100 of FIG. 1. Referring to FIGS. 1 and 3, in operation 310, the user authentication apparatus 100 identifies a first ECG signal measured from a user to be authenticated. For example, the user authentication apparatus 100 identifies the measured first ECG signal using an embedded sensor or another device.

In operation 320, the user authentication apparatus 100 determines a similarity between the first ECG signal and each of one or more second ECG signals based on the identified first ECG signal and the one or more second ECG signals included in the reference ECG signal set 110, which is a comparison target set.

In an example, the reference ECG signal set 110 includes one or more second ECG signals. For example, the reference ECG signal set 110 includes a second ECG signal initially registered by the user, includes another second ECG signal additionally registered by the user, or includes an updated second ECG signal.

The reference ECG signal set 110 stores the second ECG signal in a form of at least one of an ECG signal, a feature vector of the ECG signal, a key point extracted from the ECG signal, or in other similar forms.

The user authentication apparatus 100 determines a similarity between the first ECG signal measured from the user and the second ECG signal included in the reference ECG signal set 110. In an example, the similarity with the first ECG signal is determined based on a form in which the second ECG signal is stored.

For example, the user authentication apparatus 100 extracts a feature vector of the first ECG signal and compares a similarity between the extracted feature vector of the first ECG signal and the second ECG signal stored in the form of the feature vector. The user authentication apparatus 100 executes processing, for example, filtering, a key point extraction, and a segmentation, of the first ECG signal to correspond to the second ECG signal of which a feature vector is to be extracted, and extracts the feature vector of the first ECG signal using a trained neural network. Accordingly, the user authentication apparatus 100 determines the similarity between the first ECG signal and the second ECG signal based on the features vectors of the first ECG signal and the second ECG signal.

The user authentication apparatus 100 determines the similarity between the first ECG signal and the second ECG signal using a variety of schemes. For example, the user authentication apparatus 100 determines the similarity between the first ECG signal and the second ECG signal using a cosine distance, a cosine similarity, a Pearson correlation coefficient, a Euclid distance, a Minkowski distance, a Mahalanobis distance, and the like.

In operation 330, the user authentication apparatus 100 determines an authentication threshold corresponding to the reference ECG signal set 110.

The authentication threshold indicates a threshold of a similarity used to authenticate the first ECG signal measured from the user. In an example, the authentication threshold is a preset value or is determined based on the reference ECG signal set 110.

Referring to FIG. 1, the authentication threshold has a positive correlation with a number of second reference ECG signals included in the reference ECG signal set 110 and/or various types of second reference ECG signals. In one configuration, the authentication threshold decreases according to a decrease in the number of second ECG signals included in the reference ECG signal set 110 and/or the various types of existing second ECG signals. Alternatively, the authentication threshold increases according to an increase in the number of second ECG signals included in the reference ECG signal set 110 and/or the various types of existing second ECG signals.

Accordingly, the authentication threshold is not a static value and is a value that dynamically varies in response to updating the reference ECG signal set 110. Accordingly, the user authentication apparatus 100 determines again the authentication threshold in response to updating the reference ECG signal set 110.

In operation 340, the user authentication apparatus 100 determines whether to authenticate the first ECG signal measured from the user by comparing the determined similarity and the authentication threshold.

The user authentication apparatus 100 determines a similarity between the first ECG signal measured from the user and each of one or more second ECG signals included in the reference ECG signal set 110. For example, when one or more second ECG signals is included in the reference ECG signal set 110, the user authentication apparatus 100 determines the similarity between the first ECG signal and each of the one or more second ECG signals.

The user authentication apparatus 100 compares a maximum similarity among one or more similarities to the authentication threshold. For example, in response to the maximum similarity being less than or equal to the authentication threshold, the authentication of the first ECG signal measured from the user fails, that is, the first ECG signal is unauthenticated. In response to the maximum similarity being greater than the authentication threshold, the authentication of the first ECG signal measured from the user succeeds, that is, the first ECG signal is successfully authenticated. In addition, the user authentication apparatus 100 determines whether the first ECG signal is successfully authenticated based on the similarity and the authentication threshold.

In an example, the authentication threshold is a value that is determined based on the reference ECG signal set 110, or is a value that is determined based on a state of the user. For example, the authentication threshold is a value that is determined based on the reference ECG signal set 110 including one or more second ECG signals, or is a value that is determined based on the number and/or various types of second ECG signals.

As another example, in response to the user being in a stationary state, the user authentication apparatus 100 determines the authentication threshold using the second ECG signal, which indicates a stationary state among second ECG signal included in the reference ECG signal set 110. That is, the user authentication apparatus 100 determines the authentication threshold using the second ECG signal indicating the stationary state, instead of using the reference ECG signal set 110.

Figure 4:
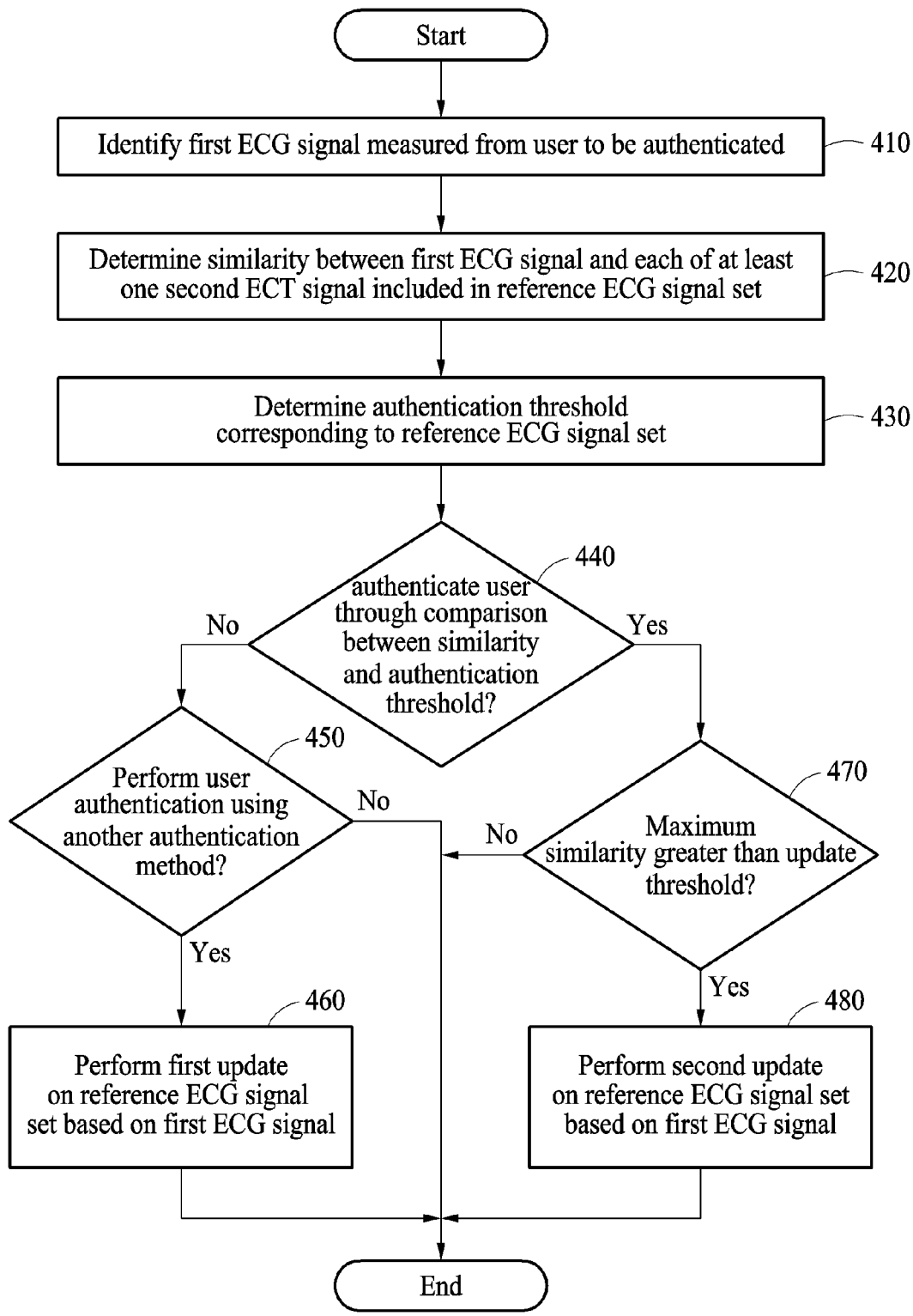
FIG. 4 is a flowchart illustrating an example of a method of updating a reference ECG signal set using a user authentication apparatus.

FIG. 4 is a flowchart illustrating an example of a method of updating a reference ECG signal set using a user authentication apparatus.

In operation 410, the user authentication apparatus 100 measures a first ECG signal of a user. For example, in response to a process or a manipulation that requires a user authentication, the user authentication apparatus 100 measures an ECG signal of the user to be authenticated. In an example, the manipulation that requires the user authentication includes a screen unlock, a payment progress, and opening of an encrypted file.

In operation 420, the user authentication apparatus 100 determines a similarity between the first ECG signal of the user and each of one or more second ECG signals included in the reference ECG signal set 110.

The user authentication apparatus 100 compares a similarity between an ECG signal, a feature vector, or an extracted key point of the first ECG signal and an ECG signal, a feature vector, or an extracted key point of the second ECG signal included in the reference ECG signal set 110.

The user authentication apparatus 100 compares a similarity in an ECG signal, a feature vector, or an extracted key point between the first ECG signal and the second ECG signal. In an example, the user authentication apparatus 100 determines the similarity between the first ECG signal and the second ECG signal using a cosine distance, a cosine similarity, a Pearson correlation coefficient, a Euclid distance, a Minkowski distance, a Mahalanobis distance, and other mathematical procedure.

In operation 430, the user authentication apparatus 100 determines an authentication threshold corresponding to the reference ECG signal set 110.

In one example, the authentication threshold is not a static value and dynamically varies. For example, the user authentication apparatus 100 determines again the authentication threshold in response to updating the reference ECG signal set 110. In detail, the authentication threshold has a positive correlation with various types and/or a number of second ECG signals.

In one example, the authentication threshold is determined to correspond to the first ECG signal. For example, in response to the first ECG signal in a stationary state being measured, the authentication threshold is determined using the second ECG signal indicating the stationary state in the reference ECG signal set 110.

In operation 440, the user authentication apparatus 100 determines whether to authenticate the first ECG signal by comparing the similarity and the authentication threshold. For example, in response to a maximum similarity among similarities being greater than the authentication threshold, the authentication of the user may succeed, that is, the user may be successfully authenticated. In response to the maximum similarity being less than or equal to the authentication threshold, the authentication of the user fails, that is, the user is unauthenticated.

Operations 410 through 440 of FIG. 4 corresponds to operations 310 through 340 of FIG. 3, and a further description related thereto may refer to the description made above related to operations 310 through 340.

In one example, a method of performing user authentication using an ECG signal and updating a reference ECG signal set includes operations 410 through 460. Hereinafter, update through operations 450 and 460 may be referred to as a first update.

In another example, a method of performing user authentication using an ECG signal and updating a reference ECG signal set includes operations 410 through 440 and 470 and 480. Hereinafter, update through operations 470 and 480 is referred to as a second update.

In response to the authentication of the first ECG signal failing, that is, in response to the first ECG signal being unauthenticated, in operation 450, the user authentication apparatus 100 performs the user authentication using another authentication method.

Prior to performing the user authentication using the other authentication method, the user authentication apparatus 100 verifies whether the first update of the reference ECG signal set 110 is performed less than a preset number of times. If the first update is performed less than the preset number of times, the user authentication apparatus 100 performs the user authentication using another authentication method excluding the ECG signal-based user authentication method.

In an example, the other authentication method excluding the ECG signal-based user authentication method includes methods of authenticating the user. For example, the user authentication is performed using a password, an iris, a fingerprint recognition, and a pattern recognition.

In response to the user being unauthenticated even using the other authentication method excluding the ECG signal-based user authentication method, the user authentication apparatus 100 displays a result as "Authentication failed" instead of performing the first update on the reference ECG signal set 110.

In response to the user being successfully authenticated using the other authentication method excluding the ECG signal-based user authentication method, the user authentication apparatus 100 displays a result as "Authentication succeeded".

In operation 460, in response to the user being successfully authenticated using the other authentication method excluding the ECG signal-based user authentication method, the user authentication apparatus 100 performs the first update on the reference ECG signal set 110. In an example, a false-rejected ECG signal is included in the reference ECG signal set 110 through the first update. The false-rejected ECG signal indicates an ECG signal in a new user state that is not included in the reference ECG signal set 110.

If a number of second ECG signals included in the reference ECG signal set 110 is less than a preset number, the user authentication apparatus 100 performs or executes the first update by adding the first ECG signal corresponding to the false-rejected ECG signal to the reference ECG signal set 110 as the second ECG signal.

In response to the number of second ECG signals included in the reference ECG signal set 110 being greater than or equal to the preset number, the user authentication apparatus 100 calculates a sum of similarities between the second ECG signals included in the existing reference ECG signal set 110. The user authentication apparatus 100 removes the second ECG signal corresponding to a maximum similarity sum and performs or executes the first update by adding the false-rejected ECG signal to the reference ECG signal set 110.

Accordingly, in response to the number of second ECG signals included in the reference ECG signal set 110 being less than the preset number, the user authentication apparatus 100 adds the false-rejected ECG signal to the reference ECG signal set 110. In response to the number of second ECG signals included in the reference ECG signal set 110 being greater than or equal to the preset number, the user authentication apparatus 100 adds the false-rejected ECG signal instead of using the second ECG signal corresponding to the maximum similarity sum between the second ECG signal and one or more other second ECG signals included in the reference ECG signal set 110.

The user authentication apparatus 100 decreases the similarity between the second ECG signals in the reference ECG signal set 110, so that the reference ECG signal set 110 includes second ECG signals corresponding to further various states.

Accordingly, the user authentication apparatus 100 performs the first update indicating the new reference ECG signal set by increasing the number of second ECG signals included in the reference ECG signal set 110 or by adding the false-rejected ECG signal instead of using the existing second ECG signal. The authentication threshold varies based on the new reference ECG signal set.

In response to the authentication of the first ECG signal succeeding, that is, in response to the first ECG signal being successfully authenticated, in operation 470, the user authentication apparatus 100 determines whether the maximum similarity determined in operation 420 is greater than an update threshold.

In an example, in operation 430, the update threshold is greater than the authentication threshold determined. The update threshold indicates a threshold used to determine whether to update the existing reference ECG signal set 110.

In response to the authentication threshold determined in operation 430 being greater than the update threshold of the existing reference ECG signal set 110, in operation 480, the user authentication apparatus 100 performs the second update on the existing reference ECG signal set 110. Alternatively, in response to the authentication threshold determined in operation 430 being less than or equal to the update threshold of the existing reference ECG signal set 110, the user authentication apparatus 100 does not perform the second update on the existing reference ECG signal set 110. Hereinafter, operation 480 of performing the second update is described.

A false sample is not included in the reference ECG signal set 110 by determining whether to perform the second update on the existing reference ECG signal set 110 using the first ECG signal of the authenticated user. In an example, the false sample represents an ECG of an unregistered user.

In operation 480, the user authentication apparatus 100 performs the second update on the existing reference ECG signal set 110 using the first ECG signal of the user measured in operation 410.

In response to the number of second ECG signals included in the reference ECG signal set 110 being less than the preset number, the user authentication apparatus 100 performs the second update by adding the authenticated first ECG signal to the reference ECG signal set 110 as the second ECG signal.

In response to the number of second ECG signals included in the reference ECG signal set 110 being greater than or equal to the preset number, the user authentication apparatus 100 calculates a similarity between the authenticated first ECG signal and each of one or more second ECG signals included in the existing reference ECG signal set 110. The user authentication apparatus 100 couples the authenticated first ECG signal and the second ECG signal indicating the maximum similarity.

Accordingly, in response to the number of second ECG signals included in the reference ECG signal set 110 being less than the preset number, the user authentication apparatus 100 adds the authenticated first ECG signal to the reference ECG signal set 110. In response to the number of second ECG signals included in the reference ECG signal set 110 being greater than or equal to the preset number, the user authentication apparatus 100 calculates a similarity between the authenticated first ECG signal and each second ECG signal included in the reference ECG signal set 110 and couples the authenticated first ECG signal and the second ECG signal indicating the maximum similarity.

Accordingly, the user authentication apparatus 100 performs or executes the first update indicating a new reference ECG signal set by increasing the number of second ECG signals included in the reference ECG signal set 110 or by adding the false-rejected ECG signal instead of using the existing second ECG signal. The authentication threshold also varies based on the new reference ECG signal set.

The user authentication apparatus 100 reflects a minute change in an ECG signal of the user by correcting the existing reference ECG signal set through the second update.

In one example, in the second update, coupling of the ECG signal is performed using a weight. For example, the user authentication apparatus 100 couples the first ECG signal and the second ECG signal corresponding to the maximum similarity based on a weight of the first ECG signal measured from the user and a weight of the second ECG signal having the maximum similarity with the first ECG signal in the reference ECG signal set 110 according to Equation 1 and Equation 2.

$$Z=(X*a+Y*b)/(a+b) \qquad \text{[Equation 1]}$$

$$c=(a^2+b^2)/(a+b) \qquad \text{[Equation 2]}$$

In these equations, X denotes the authenticated first ECG signal, Y denotes the second ECG signal having the maximum similarity with the first ECG signal, a denotes the weight of the first ECG signal, b denotes the weight of the second ECG signal, Z denotes the coupled ECG signal, and c denotes a weight of the coupled ECG signal.

In an example in which the first ECG signal and the second ECG signal are coupled, the first ECG signal and the second ECG signal are coupled based on the same form. For example, in response to the second ECG signal being stored in a form of an ECG signal itself, the first ECG signal in a form of an ECG signal itself is coupled with the second ECG signal. Also, in response to the second ECG signal being stored in a form of a feature vector, the first ECG signal is coupled with the second ECG signal using a feature vector. Also, in response to the second ECG signal being stored in a form of a key point, the first ECG signal is coupled with the second ECG signal using a key point form.

In one example, the weight of the authenticated first ECG signal represents or is indicative of a first predicted weight and a weight of the second ECG signal added to the reference ECG signal set 110 through the second update represents or is indicative of the first predicted weight.

Also, a weight of the second ECG signal added to the reference ECG signal set 110 through the first update represents or is indicative of a second predicted weight. A weight of the second ECG signal coupled through the second update is calculated according to Equation 1 and Equation 2. A weight of the second ECG signal initially registered by a registered user represents or is indicative of a third predicted weight.

In an example, the first predicted weight is less than the second predicted weight or the third predicted weight. The second predicted weight and the third predicted weight are equal to each other or differ from each other. Accordingly, the second ECG signal acquired through the first update has a relatively great weight and the reference ECG signal set 110 includes an ECG signal in a different state of the registered user.

Figure 5:
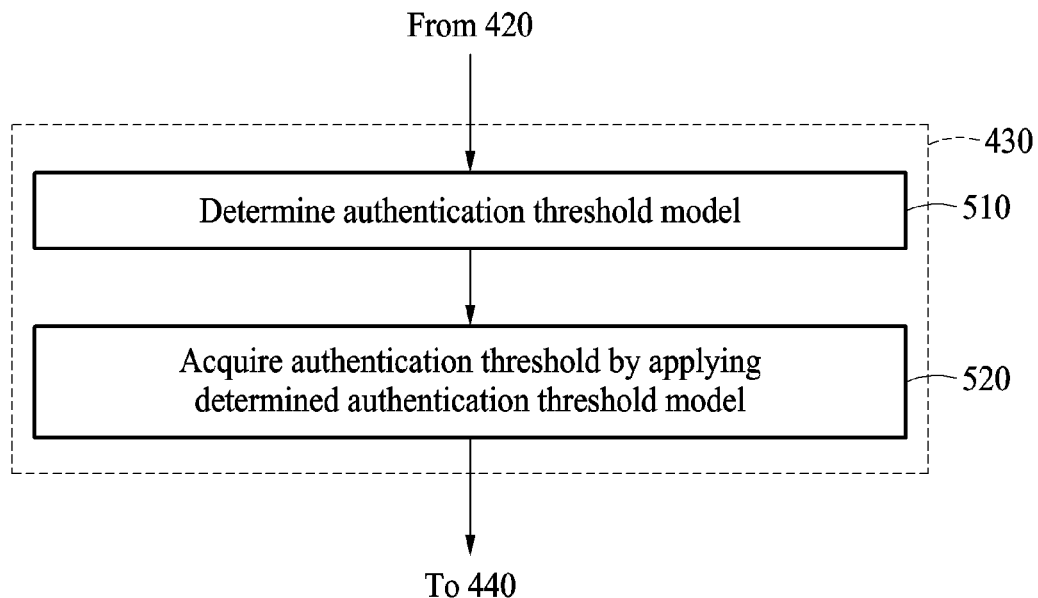
FIG. 5 is a flowchart illustrating an example of a method of determining an authentication threshold using an authentication threshold model.

FIG. 5 is a flowchart illustrating an example of a method to determine an authentication threshold using an authentication threshold model.

Referring to FIGS. 1 and 5, operation 430 performed by the user authentication apparatus 100 includes operations 510 and 520. In operation 510, the user authentication apparatus 100 determines an authentication threshold model corresponding to the existing reference ECG signal set 110.

In one example, the authentication threshold model includes one or more models. The authentication threshold model is acquired through training based on a neural network or a suitable algorithm.

For example, a first authentication threshold model is acquired through training based on a first training sample. In an example, in response to the first update being performed a preset number of times or more, the first training sample includes a feature vector of the reference ECG signal set 110 or an authentication threshold corresponding to each feature vector.

As another example, a second authentication threshold model is acquired through training based on a second training sample. In an example, in response to the first update being performed less than the preset number of times, the second training sample includes a feature vector or an authentication threshold corresponding to each feature vector corresponding to the number of second ECG signals included in the reference ECG signal set 110 being greater than or equal to the preset number.

As another example, a third authentication threshold model is acquired through training based on a third training sample. In an example, in response to the first update being performed less than the preset number of times, the third training sample includes a feature vector or an authentication threshold corresponding to each feature vector corresponding to the number of second ECG signals included in the reference ECG signal set 110 being less than the preset number.

In an example, the authentication threshold corresponding to each feature vector indicates an authentication threshold corresponding to a false rejection rate (FRR) of the reference ECG signal set 110 corresponding to each feature vector being a preset value. For example, the authentication threshold corresponding to each feature vector indicates an authentication threshold corresponding to the FRR of the reference ECG signal set 110 corresponding to each feature vector being 5%.

In an example, the feature vector of the reference ECG signal set 110 represents a feature vector for various types of second ECG signals included in the reference ECG signal set 110 and/or the number of second ECG signals included in the reference ECG signal set 110. The feature vector of the reference ECG signal set 110 represents at least one of 16 features of the reference ECG signal set 110 disclosed in the following Table 1.

For example, at least one of 16 features extracted from the existing reference ECG signal set 110 is represented as the feature vector of the existing reference ECG signal set 110. For instance, a number of remaining first updates denotes a remaining number of times acquired by subtracting a number of performed first updates from a preset number of times. The second ECG signal of the first update denotes the second ECG signal acquired through the first update and the second ECG signal of the second update denotes the second ECG signal acquired through the second update.

TABLE 1

| Number of remaining first updates | Number of second ECG signals | Number of first updated second ECG signals | Number of second updated second ECG signals |
|---|---|---|---|
| Maximum similarity between second ECG signals | Minimum similarity between second ECG signals | Average similarity between second ECG signals | Intermediate similarity between second ECG signals |
| Maximum similarity between first updated second ECG signals | Minimum similarity between first updated second ECG signals | Average similarity between first updated second ECG signals | Intermediate similarity between first updated second ECG signals |
| Maximum similarity between second updated second ECG signals | Minimum similarity between second updated second ECG signals | Average similarity between second updated second ECG signals | Intermediate similarity between second updated second ECG signals |

In operation 520, the user authentication apparatus 100 acquires the authentication threshold by applying the feature vector of the existing reference ECG signal set 110 to the authentication threshold model.

In operation 510, the user authentication apparatus 100 determines a first authentication threshold model corresponding to the first update being performed a preset number of times or more, determines a second authentication threshold model corresponding to the first update being performed less than the preset number of times and the number of second ECG signals included in the reference ECG signal set 110 being greater than or equal to a preset number. Further, the user authentication apparatus 100 determines a third authentication threshold model corresponding to the first update being performed less than the preset number of times and the number of second ECG signals included in the reference ECG signal set 110 is less than the preset number.

The user authentication apparatus 100 acquires the authentication threshold by applying the feature vector extracted through the existing reference ECG signal set 110 to the determined threshold model.

In one example, the user authentication method and the user authentication apparatus 100 update a dynamically varying authentication threshold based on the reference ECG signal set 110, and automatically update the reference ECG signal set 110. Also, the user authentication method and the user authentication apparatus 100 enhance an identification rate of ECG-signal based user authentication by including an ECG signal in a different state of a registered user in the reference ECG signal set 110.

Figure 6:
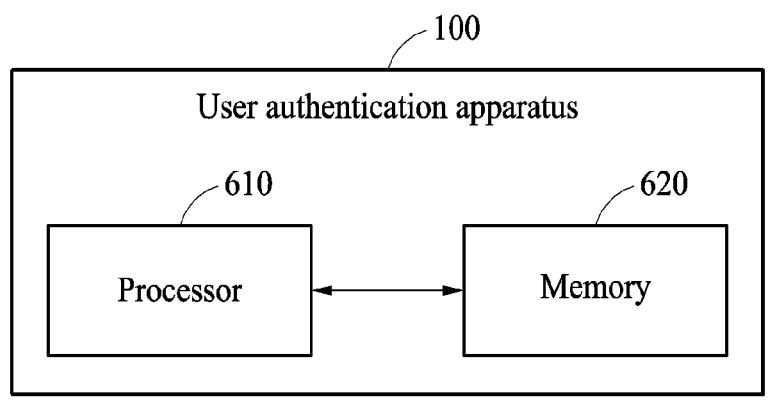
FIG. 6 is a diagram illustrating an example of a user authentication apparatus including a processor and a memory to perform user authentication.

FIG. 6 is a diagram illustrating an example of a user authentication apparatus including a processor and a memory to perform user authentication.

Referring to FIG. 6, the user authentication apparatus 100 includes a processor 610 and a memory 620. The memory 620 stores one or more instructions executable by the processor 610. The processor 610 executes the one or more instructions stored in the memory 620. By executing the instructions, the processor 610 performs one or more operations described above with FIGS. 1 through 5. The processor 610 performs a user authentication using an ECG signal in response to an instruction.

In one example, the processor 610 identifies a first ECG signal measured from a user to perform user authentication using an ECG signal of the user. The processor 610 determines a similarity between the first ECG signal and each of one or more second ECG signals based on the identified first ECG signal and one or more second ECG signals included in a reference ECG signal set that is a comparison target. The processor 610 determines an authentication threshold corresponding to the reference ECG signal set and determines whether to authenticate the first ECG signal measured from the user by comparing the determined similarity and the authentication threshold.

In one example, the processor 610 of the user authentication apparatus 100 updates the reference ECG signal set and changes the second ECG signal included in the reference ECG signal set based on the update. Accordingly, the authentication threshold dynamically varies in response to updating the reference ECG signal.

Figure 7:
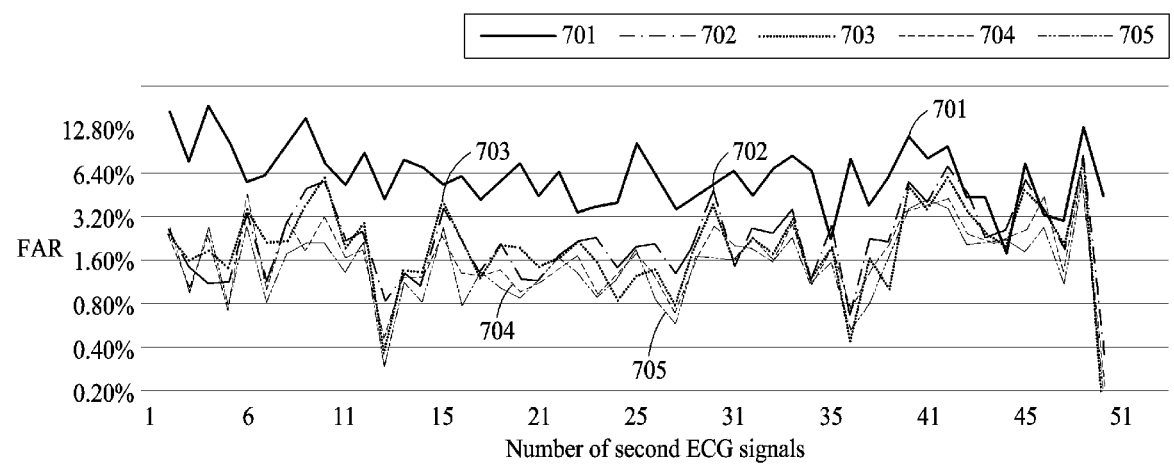
FIG. 7 illustrates an example of a test result acquired by applying an ECG signal to user authentication.

FIG. 7 illustrates an example of a test result acquired by applying an ECG signal to user authentication.

If FRR=5%, a graph 701 shows that, in response to update not being performed, an average false acceptance rate (FAR) of the user authentication apparatus 100 is 6.27%. If FRR=5%, a graph 702 shows that, in response to first update being performed using a static authentication threshold instead of a dynamically varying authentication threshold, the average FAR of the user authentication apparatus 100 is 2.41%. Alternatively, in response to FRR=5%, a graph 703 shows that, in response to first update and second update being performed using a static authentication threshold instead of the dynamically varying authentication threshold, the average FAR of the user authentication apparatus 100 is 2.22%.

In one example, in response to FRR=5%, a graph 704 shows that, in response to first update being performed using a dynamically varying authentication threshold, the average FAR of the user authentication apparatus 100 is 1.85%. Also, if FRR=5%, a graph 705 shows that, in response to first update and second update being performed using a dynamically varying authentication threshold, the average FAR of the user authentication apparatus 100 is 1.60%.

Accordingly, in the example in which the dynamically varying authentication threshold is used by performing first update and/or the second update on the reference ECG signal set, it is possible to effectively enhance an identification rate of ECG signal-based user authentication.

The user authentication apparatus, and other apparatuses, units, modules, devices, and other components described herein are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 3-5 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and providing the instructions or software and any associated data, data files, and data structures to a processor or computer so that the processor or computer can execute the instructions.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are coupled in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of authenticating a user, comprising:
   identifying a first electrocardiogram (ECG) signal measured from the user;
   determining a similarity between the first ECG signal and a second ECG signal based on the identified first ECG signal and the second ECG signal included in a reference ECG signal set;

determining an authentication threshold, based on a state of the user, corresponding to the reference ECG signal set; and determining whether to authenticate the first ECG signal measured from the user by comparing the determined similarity and the authentication threshold, whether the reference ECG signal set is updated using the first ECG signal, when the authentication with respect to the first ECG signal is a success.

2. The method of claim 1, wherein the determining of the authentication threshold comprises:

determining an authentication threshold model corresponding to the reference ECG signal set; and acquiring the authentication threshold by applying a feature vector of the reference ECG signal set to the determined authentication threshold model.

3. The method of claim 2, wherein the feature vector is extracted from the preprocessed second ECG signal through a neural network.

4. The method of claim 2, wherein the authentication threshold has a positive correlation with any one or any combination of a number of second ECG signals included in the reference ECG signal set.

5. The method of claim 1, wherein the determining of whether to authenticate comprises determining that an authentication is a success in response to a maximum similarity among the one or more similarities being greater than the authentication threshold, or determining that the authentication is a failure in response to the maximum similarity being less than or equal to the authentication threshold.

6. The method of claim 5, further comprising:

updating the reference ECG signal set in response to the authentication being determined as the success, wherein the updating comprises updating the reference ECG signal set using the first ECG signal in response to the maximum similarity being greater than an update threshold of the reference ECG signal set.

7. A method of authenticating a user, comprising:

identifying a first electrocardiogram (ECG) signal measured from the user;

determining a similarity between the first ECG signal and a second ECG signal based on the identified first ECG signal and the second ECG signal included in a reference ECG signal set;

determining an authentication threshold, based on a state of the user, corresponding to the reference ECG signal set;

determining whether to authenticate the first ECG signal measured from the user by comparing the determined similarity and the authentication threshold, wherein the determining of whether to authenticate comprises determining that an authentication is a success in response to a maximum similarity among the one or more similarities being greater than the authentication threshold, or determining that the authentication is a failure in response to the maximum similarity being less than or equal to the authentication threshold; and updating the reference ECG signal set in response to the authentication being determined as the failure, wherein the updating comprises updating the reference ECG signal set using the first ECG signal in response to the user being authenticated using an authentication method excluding an ECG signal-based user authentication.

8. The method of claim 7, wherein the authentication of the user by the authentication method excluding the ECG signal-based user authentication is performed in response to a number of updates being less than a preset threshold.

9. The method of claim 6, wherein the updating of the reference ECG signal set using the first ECG signal comprises adding the authenticated first ECG signal to the reference ECG signal set as the second ECG signal in response to a number of second ECG signals included in the reference ECG signal set being less than a preset number, or coupling the measured first ECG signal and the second ECG signal indicating the maximum similarity in response to the number of second ECG signals included in the reference ECG signal set being greater than or equal to the preset number.

10. The method of claim 7, wherein the updating of the reference ECG signal set using the first ECG signal comprises adding the unauthenticated first ECG signal to the reference ECG signal set as the second ECG signal in response to a number of second ECG signals included in the reference ECG signal set being less than a preset number, or adding the first ECG signal to the reference ECG signal set instead of using the second ECG signal corresponding to a maximum similarity sum between the second ECG signal and other second ECG signals included in the reference ECG signal set in response to the number of second ECG signals included in the reference ECG signal set being greater than or equal to the preset number.

11. The method of claim 9, wherein the coupling comprises coupling the first ECG signal and the second ECG signal based on a weight of the first ECG signal and a weight of the second ECG signal having a maximum similarity with the first ECG signal in the reference ECG signal set.

12. A non-transitory computer-readable storage medium storing instructions that, when executed by a processor, cause the processor to perform the method of claim 1.

13. An apparatus to authenticate a user, comprising:

a processor; and a memory configured to store one or more instructions executable by the processor, wherein, when the one or more instructions is executed by the processor, the processor is configured to identify a first electrocardiogram (ECG) signal measured from the user, determine a similarity between the first ECG signal and a second ECG signal based on the identified first ECG signal and the second ECG signal included in a reference ECG signal set, determine an authentication threshold, based on a state of the user, corresponding to the reference ECG signal set, and determine whether to authenticate the first ECG signal measured from the user by comparing the determined similarity and the authentication threshold, whether the reference ECG signal set is updated using the first ECG signal, when the authentication with respect to the first ECG signal is a success.

14. The apparatus of claim 13, wherein the processor is configured to determine an authentication threshold model corresponding to the reference ECG signal set, and to acquire the authentication threshold by applying a feature vector of the reference ECG signal set to the determined authentication threshold model.

15. The apparatus of claim 14, wherein the authentication threshold has a positive correlation with any one or any combination of a number of second ECG signals included in the reference ECG signal set.

16. The apparatus of claim 13, wherein the processor is configured to determine that an authentication is a success in response to a maximum similarity among the one or more similarities being greater than the authentication threshold, or to determine that the authentication is a failure in response to the maximum similarity being less than or equal to the authentication threshold.

17. The apparatus of claim 16, wherein the processor is configured to update the reference ECG signal set in response to the authentication being determined as the success, and to update the reference ECG signal set using the first ECG signal in response to the maximum similarity being greater than an update threshold of the reference ECG signal set.

18. The apparatus of claim 16, wherein the processor is configured to update the reference ECG signal set in response to the authentication being determined as the failure, and to update the reference ECG signal set using the first ECG signal in response to the user being authenticated using an authentication method excluding an ECG signal-based user authentication.

19. The apparatus of claim 17, wherein, in the case of updating the reference ECG signal set using the first ECG signal, the processor is configured to add the authenticated first ECG signal to the reference ECG signal set as the second ECG signal in response to a number of second ECG signals included in the reference ECG signal set being less than a preset number, or couple the measured first ECG signal and the second ECG signal indicating the maximum similarity in response to the number of second ECG signals included in the reference ECG signal set being greater than or equal to the preset number.

20. The apparatus of claim 18, wherein, in the case of updating the reference ECG signal set using the first ECG signal, the processor is configured to add the unauthenticated first ECG signal to the reference ECG signal set as the second ECG signal in response to a number of second ECG signals included in the reference ECG signal set being less than a preset number, or to add the first ECG signal to the reference ECG signal set instead of using the second ECG signal corresponding to a maximum similarity sum between the second ECG signal and other second ECG signals included in the reference ECG signal set in response to the number of second ECG signals included in the reference ECG signal set being greater than or equal to the preset number.

* * * * *